United States Patent [19]

Inoue et al.

[11] 4,452,719
[45] Jun. 5, 1984

[54] 4-(TRANS-4'-ALKYLOXYMETHYLCYCLOHEXYL)BENZOIC ACID ESTERS

[75] Inventors: Hiromichi Inoue; Takashi Inukai; Yasuyuki Goto, all of Kanagawaken, Japan

[73] Assignee: Chisso Corporation, Osaka, Japan

[21] Appl. No.: 493,288

[22] Filed: May 10, 1983

[30] Foreign Application Priority Data

May 11, 1982 [JP] Japan .................................. 57-78737

[51] Int. Cl.$^3$ ........................ C09K 3/34; C07C 69/78; C07C 121/75
[52] U.S. Cl. .......................... 252/299.63; 260/465 D; 560/59
[58] Field of Search ..................... 260/465 D; 560/59; 252/299.63

[56] References Cited

U.S. PATENT DOCUMENTS 4,229,315 10/1980 Krause et al. .............. 260/465 D X
4,387,038 6/1983 Fukuri et al. ................. 252/299.63

*Primary Examiner*—Dolph H. Torrence
*Attorney, Agent, or Firm*—Fred Philpitt

[57] ABSTRACT

Novel liquid crystal compounds which are useful as a component constituting liquid crystal compositions and particularly capable of broadening the liquid crystal temperature range of the compositions due to high clearing point of the compounds, and liquid crystal compositions comprising the same, are provided, which compounds are 4-(trans-4'-alkyloxymethylcyclohexyl)-benzoic acid esters having the general formula

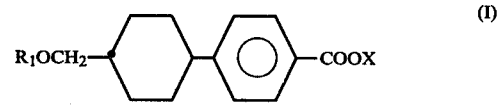

wherein X represents

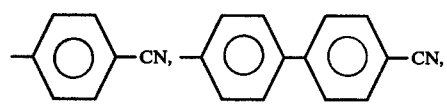

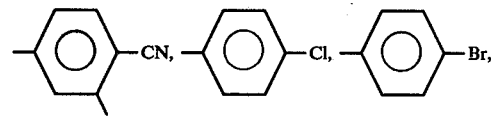

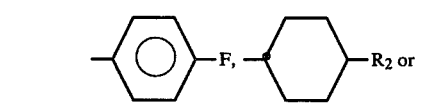

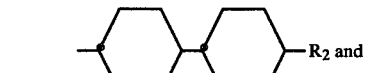
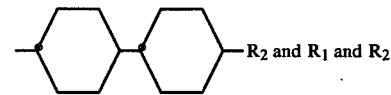

each represent an alkyl group of 1 to 10 carbon atoms.

6 Claims, No Drawings

4-(TRANS-4'-ALKYLOXYMETHYLCYCLOHEX-YL)BENZOIC ACID ESTERS

BACKGROUND OF THE INVENTION

This invention relates to novel compounds exhibiting a liquid crystal phase and liquid crystal compositions comprising the same.

Liquid crystal display elements are obtained by utilizing the optical anisotropy and dielectric anisotropy of liquid crystal substances, and if those which have now been practically used are classified in a principle manner, TN type (twisted nematic type), DS type (dynamic scattering type), guest-host type, PC type (phase transition type), DAP type, etc. are representative. Properties of liquid crystal substances suitable to the uses of the respective types vary, but any of the liquid crystal substances are common in that they require stabilities to moisture, air and physical effects such as heat, radiations at infrared part, visible part and ultraviolet part, and continuous and alternate electric field. Further, as commercially usable liquid crystal materials, those which can be existent in the form of liquid crystal phase at a temperature range of 0° C. to 60° C. are preferred. Furthermore, there are the optimal values of physical properties which vary depending on the kinds of display elements (anistropy of dielectric constant and anisotropy of refractive index). In the present status, no single compound which satisfies these various performances is present, and liquid crystal compositions obtained by mixing some kinds of liquid-crystalline compounds or non-liquid-crystalline compounds have been practically used.

The object of the present invention is to provide compounds which are useful as a component constituting such liquid crystal compositions and particularly capable of broadening their liquid crystal temperature range due to high clearing point of the compounds.

SUMMARY OF THE INVENTION

The present invention resides in esters derived from 4-(trans-4'-alkyloxymethylcyclohexyl)benzoic acid and having the general formula

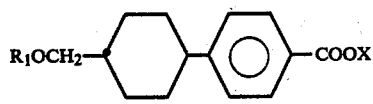

(I)

wherein X represents

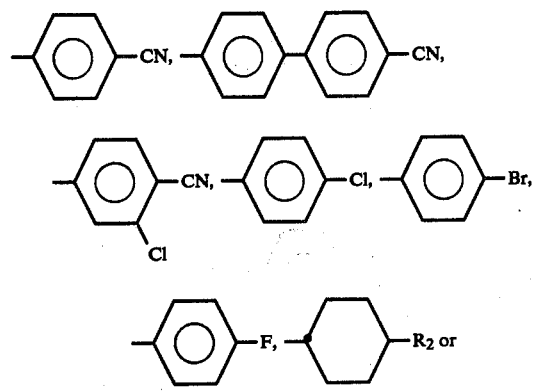

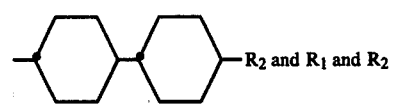

$R_2$ and $R_1$ and $R_2$ each represent an alkyl group of 1 to 10 carbon atoms.

The esters are concretely classified into those having the following 4 general formulas:

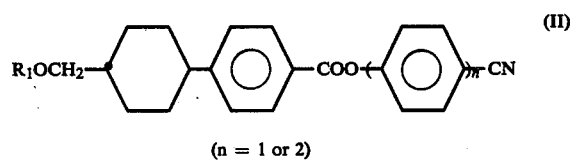

(II)

(n = 1 or 2)

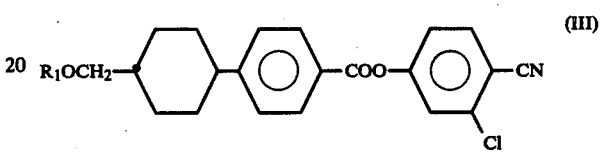

(III)

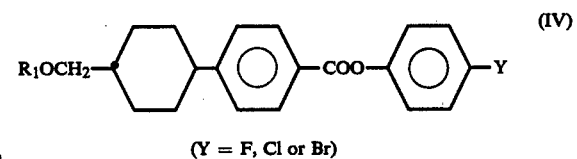

(IV)

(Y = F, Cl or Br)

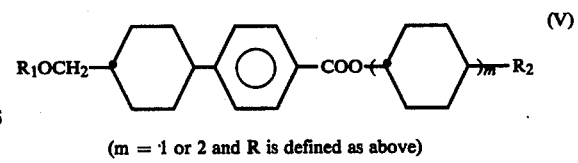

(V)

(m = 1 or 2 and R is defined as above)

DESCRIPTION OF THE PREFERRED EMBODIMENTS

Any of the compounds of the present invention have a broad nematic temperature range, but since the temperatures within the range are high, if the compounds are singly used, their practical usability as a liquid crystal material for display elements are limited. On the other hand, since they have a superior compatability with other liquid crystal compounds and also have a high clearing point (N-I point), if they are mixed with one kind of or a mixture of some kinds of other liquid crystal substances such as Sciff's base system, azoxy system, benzoic acid phenyl ester system, cyclohexanecarboxylic acid phenyl ester system, cyclohexanecarboxylic acid cyclohexane ester system, biphenyl system, phenylcyclohexane system, phenylpyridine system, phenylmetadioxane system, etc., then they are useful as the so-called high temperature liquid crystal component for elevating their clearing points.

Among the compounds of the present invention, those of the formulas (II) and (III) exhibit a strong positive dielectric anisotropy. Thus, when they are added to a liquid crystal compound having a negative dielectric anisotropy, it is possible to obtain a liquid crystal composition having a positive dielectric anisotropy, and when they are added to a liquid crystal compound having a positive dielectric anisotropy, it is also possible to make lower the threshold voltage of its electrooptical response.

Further, the compounds of the formula (IV) exhibit a weaker positive dielectric anisotropy than those of the compounds of the formulas (II) and (III), and are used adding them to a liquid crystal compound having a negative or positive dielectric anisotropy as in the case of the compounds of the formulas (II) and (III); particularly when they are added to a liquid crystal compound having a larger value of positive dielectric anisotropy than those of the compounds of the formula (IV) themselves, it is possible to reduce its threshold voltage value (see Examples 61 and 62 mentioned below).

Furthermore, the compounds of the formula (V) exhibit a weak negative dielectric anisotropy and are used as a component of a liquid crystal composition having a positive dielectric anisotropy or a liquid crystal composition having a negative dielectric anisotropy, and particularly when they are added to a liquid crystal having a positive dielectric anisotropy, they are suitable for broadening its liquid crystal temperature range. In general, a liquid crystal component which broadens the liquid crystal temperature range of a liquid crystal composition comprising the component, particularly the upper limit of the range, is liable to increase the viscosity of the composition, but in the case where the compounds of the formula (V) are added, such a bad effect is relatively little and the threshold voltage and saturation voltage in response of TN type display elements show only a very slight increase (see Examples 62 and 63). The thus obtained liquid crystal compositions having a positive dielectric anisotropy can be applied, utilizing their optical anisotropy and dielectric anisotropy, to display elements using a nematic liquid crystal of a twisted liquid crystal arrangement (the so-called TN cell), color display elements having a guest-host effect applied, phase change type display elements (PC type), etc. Further, liquid crystal compositions having a negative dielectric anisotropy, obtained as above, can be applied to display elements of DS type (dynamic scattering type), DAP type, guest-host type, PC type, etc.

Next, the preparation steps of the compounds of the formula (I) of the present invention will be described below. First, 4-(trans-4'-alkyloxymethylcyclohexyl)-benzoic acid chlorides as common intermediates are preferably prepared by way of the following steps: First, known trans-4-phenylcyclohexanecarboxylic acid methyl ester (see W. S. Johnson et al, J.A.C.S. 67, 1045 (1945)) (A) is reduced with lithium aluminum hydride (LiAlH$_4$) or the like to obtain trans-4-phenylcyclohexylmethanol (B), which is then reacted with p-toluenesulfonyl chloride in dry pyridine to obtain p-toluenesulfonic acid trans-4-phenylcyclohexylmethyl (C), which is then reacted with an alcoholate to obtain a trans-4-alkyloxymethyl-1-phenylcyclohexane (D), which is then heated together with iodine and iodic acid to obtain a 4-(trans-4'-alkyloxymethylcyclohexyl)iodobenzene (E), which is then reacted with a cyanogenating agent such as cuprous cyanide to obtain a 4-(trans-4'-alkyloxymethylcyclohexyl)benzonitrile (F), which is then hydrolyzed by heating it together with KOH or the like in a solvent to obtain a 4-(trans-4'-alkyloxymethylcyclohexyl)benzoic acid (G), which is then reacted with a chlorinating agent such as thionyl chloride, phosphorus pentachloride, etc. to obtain an acid chloride (H). These steps are illustrated by the following chart:

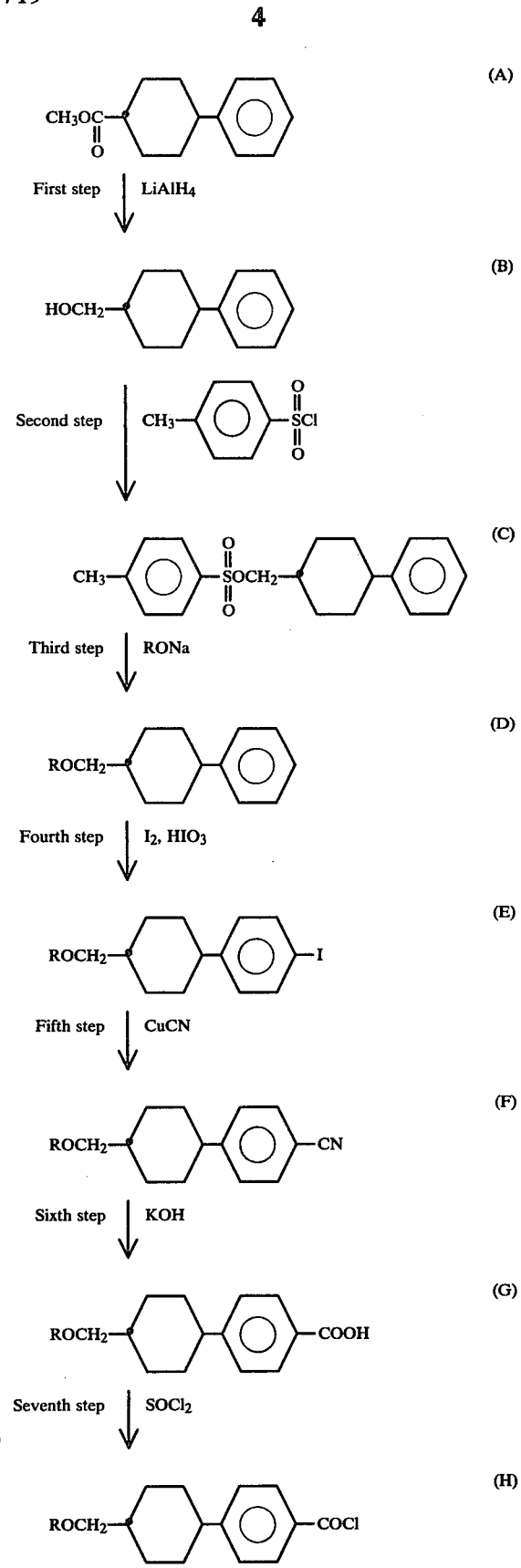

In the third step of this chart, when the compound (C) is reacted with, as an alcoholate, sodium methoxide, sodium ethoxide, sodium propoxide, sodium butoxide, sodium pentoxide, sodium hexyloxide, sodium heptyloxide or sodium octyloxide, there are obtained compounds of the formula (H) wherein R is $CH_3$, $C_2H_5$, $C_3H_7$, $C_4H_9$, $C_5H_{11}$, $C_6H_{13}$, $C_7H_{15}$ or $C_8H_{17}$. When the thus obtained compounds of the formula (H) are reacted with a phenol corresponding to the final product aimed, the ester compounds of the formula (I) are easily obtained. Namely, when the compounds of the formula (H) are reacted with 4-cyanophenol, 4-hydroxy-4'-cyanobiphenyl, 3-chlor-4-cyanophenol, 4-halogenophenol, 4-trans-alkylcyclohexanol or 4-trans-(4'-trans-alkylcyclohexyl)-cyclohexanol, compounds of the formula (II) wherein $n=1$, the formula (II) wherein $n=2$, the formula (III) wherein $n=1$, the formula (IV) wherein $n=1$, the formula (V) wherein $n=1$ or the formula (V) wherein $n=2$ are obtained.

The preparation of the compounds of the present invention, their properties and the details of their use as liquid crystal materials will be described below.

EXAMPLE 1

Preparation of 4-(trans-4'-methyloxymethylcyclohexyl)benzoic acid 4"-cyanophenyl ester (a compound of the formula (II) wherein $n=1$ and $R=CH_3$)

First Step

Dry tetrahydrofuran (THF) (420 ml) was added to lithiumaluminum hydride (11.1 g, 0.293 mol) and the mixture was vigorously agitated, followed by dropwise adding to the mixture, a solution obtained by dissolving trans-4-phenylcyclohexanecarboxylic acid methyl ester (II) (64.0 g, 0.293 mol) in THF (70 ml), while keeping the reaction temperature at 20° C. or lower. After completion of the dropwise addition, the reaction mixture was warmed up to 55° C., reacted for 2 hours and cooled, followed by adding ethyl acetate (12 ml) and water (100 ml), and then adding 18% sulfuric acid (350 ml) to form two separated layers of a tetrahydrofuran layer and an aqueous layer. n-Heptane (200 ml) was added to the former layer and the mixture was transferred into a separating funnel, followed by washing with water (500 ml), washing with 2% aqueous solution of sodium carbonate (500 ml), further washing with water till the aqueous layer became neutral, distilling off n-heptane and THF, recrystallizing solid as still residue from n-heptane (20 ml), filtering off the resulting crystals and drying to obtain 4-phenylcyclohexylmethanol (III) (51.4 g). M.P. 47.3°~48.5° C.

Second Step

Compound (B) (50 g, 0.268 mol) obtained in the first step was dissolved in pyridine (110 ml) and cooled to 5° C. or lower. To the solution was dropwise added through a dropping funnel, a solution obtained by dissolving p-toluenesulfonic acid chloride (50.1 g, 0.268 mol) in dry pyridine (70 ml), so that the reaction temperature did not exceed 10° C. After the dropwise addition, a cooling bath used in the addition was removed, and the mixture was agitated at room temperature for 4 hours, followed by adding water (100 ml) and toluene (300 ml), agitating the mixture, transfering it into a separating funnel, washing the resulting toluene layer twice with 6N-HCl aqueous solution (100 ml), once with water (200 ml), further twice with 2N-NaOH aqueous solution (100 ml), and four time with water (200 ml), distilling off toluene under reduced pressure, recrystallizing the resulting crystals from toluene (90 ml), filtering off and drying to obtain p-toluenesulfonic acid trans-4-phenylcyclohexylmethyl (C) (77.0 g). M.P. 108.0°~108.7° C.

Third Step

Slices of metal sodium (17.4 g, 0.755 mol) were added in small portions to methyl alcohol (250 ml) agitated at room temperature, to prepare sodium methoxide. After metal sodium pieces disappeared, a solution obtained by dissolving compound (C) (200.0 g, 0.581 mol) previously obtained, in dry toluene (600 ml) was gradually added through a dropping funnel so that the inner temperature was kept in the range of 50°~60° C. After the dropwise addition, the mixture was refluxed for 4 hours and then cooled, followed by adding water (20 ml), transfering the mixture into a separating funnel, washing separated toluene layer with water till the aqueous layer became neutral, distilling off toluene under reduced pressure, distilling the residue under reduced pressure, and collecting a fraction having a boiling point of 105°~108° C./1.5 mmHg to obtain trans-4-methyloxymethyl-1-phenylcyclohexane (D) (100.0 g).

Fourth Step

Into a 1 l three-neck flask were added compound (D) (100.0 g, 0.489 mol), acetic acid (344 ml), water (91 ml), iodic acid (20.6 g, 0.117 mol), iodine (54.5 g, 0.215 mol), $CCl_4$ (40 ml) and conc. hydrochloric acid (14 ml), followed by stirring and further refluxing for 3 hours while heating on a mantle heater. After cooling, a 10% aqueous solution of sodium thiosulfate (15 ml) was added to cause the color of excess iodine to disappear, followed by adding n-heptane (200 ml), transferring the mixture into a separating funnel, washing the resulting n-heptane layer with water till the aqueous layer becomes neutral, distilling off n-heptane under reduced pressure, dissolving the residue in n-hexane (50 ml), allowing the solution to stand at $-10°$ to $-20°$ C. for 12 hours, filtering off the resulting crystals and drying to obtain 4-(trans-4'-methyloxymethylcyclohexyl)iodobenzene (E) (81.3 g). M.P. 40.3°~42.3° C.

Fifth Step

Into a 300 ml three-neck flask were added compound (E) (20.0 g, 0.061 mol), cuprous cyanide (6.3 g, 0.071 mol) and N,N-dimethylformamide (DMF) (63 ml). The mixture was agitated and refluxed for 6 hours while heating on a mantle heater. After completion of the reaction, the reaction mixture was cooled down to room temperature and a 28% aqueous ammonia (18 ml) was added, followed by agitating the mixture, adding n-heptane (50 ml) for extraction, filtering off an insoluble matter in the n-heptane layer, washing the layer with 6N-HCl (50 ml), further washing with water till the aqueous layer became neutral, concentrating under reduced pressure, recrystallizing the resulting raw crystals from ethanol (10 ml), filtering off and drying to obtain 4-(trans-4'-methyloxymethylcyclohexyl)benzonitrile (F) (6.4 g).

Sixth Step

Into a 2 l three-neck flask were added compound (F) (25 g, 0.109 mol) obtained in the fifth step and ethylene glycol (722 ml) and further an aqueous solution obtained by dissolving KOH (18.8 g, 0.335 mol) in water (26 ml), followed by refluxing the mixture for 12 hours while heating on a mantle heater. After cooling, the reaction mixture was acidified by adding 6N-HCl (200 ml) to form crystals, which were filtered off and dried, followed by dissolving the crystals in ethanol (200 ml) and recrystallizing to obtain 4-(trans-4'-methyloxymethylcyclohexyl)benzoic acid (G) (18.8 g). This had a melting point (C-N point) of 132.7° C. and a clearing point (N-I point) of 234.6° C.

Seventh Step

Thionyl chloride (20 ml) was added to compound (G) (18.8 g, 0.076 mol) obtained in the sixth step, and the mixture was heated at 60° to 80° C. for 4 hours on a water bath. After the reaction mixture became uniform, it was allowed to stand further for one hour, followed by completely distilling off excess thionyl chloride. The resulting oily substance as residue is 4-(trans-4'-methyloxymethylcyclohexyl)benzoic acid chloride (H).

Eighth Step

Compound (H) (1 g, 0.004 mol) obtained in the seventh step was added with vigorous shaking to a solution obtained by dissolving 4-cyanophenol (0.5 g, 0.004 mol) in dry pyridine (2 ml). The reaction liquid was allowed to stand over night, followed by adding water (10 ml), further adding toluene (50 ml) for extraction, washing the resulting toluene layer with 6N-HCl, further with 2N-NaOH aqueous solution, washing with water till the aqueous layer became neutral, distilling off toluene under reduced pressure, recrystallizing the resulting raw crystals from ethanol (50 ml), filtering off and drying to obtain objective 4-(trans-4'-methyloxymethylcyclohexyl)benzoic acid 4''-cyanophenyl ester (0.5 g), having a melting point (C-N point) of 130.7° C. and a clearing point (N-I point) of 230.6° C. Further, the elemental analysis values of this compound accorded well with its calculated values as follows:

|   | Observed value (%) | Calculated value (%) (in terms of $C_{22}H_{23}NO_3$) |
|---|---|---|
| C | 75.6 | 75.62 |
| H | 6.6 | 6.63 |
| N | 4.0 | 4.01 |

EXAMPLE 2

Preparation of 4-(trans-4'-methyloxymethyl)benzoic acid 4''-cyano-4''-biphenyl ester (a compound of the formula (II) wherein $R = CH_3$)

4-(Trans-4'-methyloxymethylcyclohexyl)benzoic acid chloride (1 g, 0.004 mol) obtained in the seventh step of Example 1 was added to a solution obtained by dissolving 4-hydroxy-4'-cyanobiphenyl (0.8 g, 0.004 mol) in dry pyridine (5 ml) to react the mixture to obtain the compound above captioned (0.6 g). This compound had a melting point (C-N point) of 180.2° C. and a clearing point (N-I point) of 280° C. or higher. Its precise measurement was difficult, but when it was mixed with a liquid crystal of cyanobiphenyl system and its clearing point was sought by extrapolation, the point was found to be 330° C. The elemental analysis values of the compound accorded well with its calculated values as follows:

|   | Observed value (%) | Calculated value (%) (in terms of $C_{28}C_{27}NO_3$) |
|---|---|---|
| C | 79.0 | 79.03 |
| H | 6.3 | 6.40 |
| N | 3.3 | 3.29 |

EXAMPLES 3~56

Example 1 was repeated except that 4-cyanophenol of Example 1 was replaced by various kinds of phenols, to prepare the following compounds. The phase transition temperatures of these compounds are shown in Table 1 together with those of Examples 1 and 2.

In the column of phase transition point in Table 1, C, S, N and I represent crystalline phase smectic phase, nematic phase and isotropic phase, respectively; and a symbol "." shows that the phase captioned above (C, S, N or I) is present and a symbol "—" shows that the phase is absent, and the numeral values between the respective phases represent the respective transition points between the respective phases.

TABLE 1

| Compound No. | Formula | Substituent in general formula n | m | $R_1$ | $R_2$ | Y | Phase transition point (°C.) C | S | N | I | |
|---|---|---|---|---|---|---|---|---|---|---|---|
| 1 | (II) | 1 | — | $CH_3$ | — | — | . 130.7 | — | . 230.6 | . | Example |
| 2 | | 1 | — | $C_2H_5$ | — | — | . 119.5 | — | . 204 | . | |
| 3 | | 1 | — | $C_3H_7$ | — | — | . 81.5 | — | . 187 | . | |
| 4 | | 2 | — | $CH_3$ | — | — | . 180.2 | — | . 330* | . | Example |
| 5 | | 2 | — | $C_2H_5$ | — | — | . 143.5 | — | . 329* | . | |
| 6 | | 2 | — | $C_3H_7$ | — | — | . 109 | — | . 311* | . | |
| 7 | (III) | — | — | $CH_3$ | — | — | . 99.4 | — | . 137.0 | . | |
| 8 | | — | — | $C_2H_5$ | — | — | . 93 | — | . 103.6 | . | |
| 9 | | — | — | $C_3H_7$ | — | — | . 76 | — | . 89.8 | . | |
| 10 | | — | — | $C_5H_{11}$ | — | — | . 58 | — | . 64.1 | . | |
| 11 | (IV) | — | — | $CH_3$ | — | Br | . 130.4 | — | . 174.5 | . | |
| 12 | | — | — | $CH_3$ | — | Cl | . 130 | — | . 178.4 | . | |
| 13 | | — | — | $CH_3$ | — | F | . 112.6 | — | . 151.1 | . | |
| 14 | | — | — | $C_2H_5$ | — | Br | . 96.7 | — | . 150.2 | . | |
| 15 | (IV) | — | — | $C_2H_5$ | — | Cl | . 97.8 | — | . 155.1 | . | |
| 16 | | — | — | $C_2H_5$ | — | F | . 96.6 | — | . 128.5 | . | |
| 17 | | — | — | $C_3H_7$ | — | Br | . 93.5 | — | . 143.6 | . | |
| 18 | | — | — | $C_3H_7$ | — | Cl | . 87.4 | — | . 146.4 | . | |
| 19 | | — | — | $C_3H_7$ | — | F | . 81.8 | — | . 118.8 | . | |
| 20 | | — | — | $C_4H_9$ | — | Br | . 71 | . 85.4 | . 122.0 | . | |
| 21 | | — | — | $C_4H_9$ | — | Cl | . 67 | . 77.3 | . 125.8 | . | |
| 22 | | — | — | $C_4H_9$ | — | F | . 66.5 | — | . 98.2 | . | |
| 23 | | — | — | $C_5H_{11}$ | — | Br | . 68.3 | . 88.4 | . 121.6 | . | |
| 24 | | — | — | $C_5H_{11}$ | — | Cl | . 77.0 | . 79.3 | . 121.7 | . | |
| 25 | | — | — | $C_5H_{11}$ | — | F | . 57.8 | — | . 89.8 | . | |
| 26 | (V) | — | 1 | $CH_3$ | $CH_3$ | — | . 89.2 | — | . 113.8 | . | |
| 27 | | — | 1 | $CH_3$ | $C_2H_5$ | — | . 78.3 | — | . 118.5 | . | |

TABLE 1-continued

| Compound No. | Formula | \_ n | m | $R_1$ | $R_2$ | Y | C | S | N | I |
|---|---|---|---|---|---|---|---|---|---|---|
| 28 | | — | 1 | $CH_3$ | $C_3H_7$ | — | . 109.5 | — | . 141.0 | . |
| 29 | | — | 1 | $CH_3$ | $C_4H_9$ | — | . 82.1 | — | . 132.8 | . |
| 30 | | — | 1 | $CH_3$ | $C_5H_{11}$ | — | . 92.4 | — | . 139.7 | . |
| 31 | | — | 1 | $CH_3$ | $C_6H_{13}$ | — | . 75.7 | — | . 131.5 | . |
| 32 | | — | 1 | $CH_3$ | $C_7H_{15}$ | — | . 87.1 | — | . 133.4 | . |
| 33 | | — | 1 | $C_2H_5$ | $CH_3$ | — | . 78.3 | — | . 118.4 | . |
| 34 | | — | 1 | $C_2H_5$ | $C_2H_5$ | — | . 58.6 | — | . 88.3 | . |
| 35 | | — | 1 | $C_2H_5$ | $C_3H_7$ | — | . 65.1 | — | . 119.3 | . |
| 36 | | — | 1 | $C_2H_5$ | $C_4H_9$ | — | . 73.5 | — | . 112.1 | . |
| 37 | | — | 1 | $C_2H_5$ | $C_5H_{11}$ | — | . 61.6 | — | . 123.0 | . |
| 38 | | — | 1 | $C_2H_5$ | $C_6H_{13}$ | — | . 60.6 | — | . 115.7 | . |
| 39 | | — | 1 | $C_2H_5$ | $C_7H_{15}$ | — | . 63.0 | — | . 118.2 | . |
| 40 | | — | 1 | $C_3H_7$ | $C_2H_5$ | — | . 39.0 | — | . 83.8 | . |
| 41 | | — | 1 | $C_3H_7$ | $C_3H_7$ | — | . 54.3 | — | . 110.8 | . |
| 42 | | — | 1 | $C_3H_7$ | $C_4H_9$ | — | . 54.5 | — | . 104.5 | . |
| 43 | | — | 1 | $C_3H_7$ | $C_6H_{13}$ | — | . 53.9 | — | . 105.5 | . |
| 44 | | — | 1 | $C_3H_7$ | $C_7H_{15}$ | — | . 59.7 | — | . 112.9 | . |
| 45 | | — | 2 | $CH_3$ | $C_2H_5$ | — | . 76.5 | . 96.0 | . 280.1 | . |
| 46 | | — | 2 | $CH_3$ | $C_3H_7$ | — | . 102.4 | . 104.4 | . 270.8 | . |
| 47 | | — | 2 | $CH_3$ | $C_4H_9$ | — | . 82.0 | . 97.8 | . 280.3 | . |
| 48 | | — | 2 | $CH_3$ | $C_5H_{11}$ | — | . 80.0 | . 131.1 | . 285.6 | . |
| 49 | | — | 2 | $C_2H_5$ | $C_2H_5$ | — | . 64.5 | . 76.7 | . 265.8 | . |
| 50 | | — | 2 | $C_2H_5$ | $C_3H_7$ | — | . 65.8 | . 78.4 | . 286.9 | . |
| 51 | | — | 2 | $C_2H_5$ | $C_4H_9$ | — | . 67.0 | . 131.3 | . 277.5 | . |
| 52 | | — | 2 | $C_2H_5$ | $C_5H_{11}$ | — | . 66.5 | . 157.3 | . 275.3 | . |
| 53 | | — | 2 | $C_3H_7$ | $C_2H_5$ | — | . 55.0 | . 61.1 | . 249.8 | . |
| 54 | | — | 2 | $C_3H_7$ | $C_3H_7$ | — | . 56.2 | . 99.1 | . 257.8 | . |
| 55 | | — | 2 | $C_3H_7$ | $C_4H_9$ | — | . 57.5 | . 141.8 | . 265.6 | . |
| 56 | | — | 2 | $C_3H_7$ | $C_5H_{11}$ | — | . 57.0 | . 164.7 | . 264.4 | . |

*Values obtained by extrapolation method.

EXAMPLES 57~63 (USE EXAMPLES)

Use examples of compounds optionally selected from the group of the compounds of the present invention as a component of a liquid crystal composition will be described below. The effectiveness of the compounds of the present invention will be most readily understood by showing what improvement in specific properties is exhibited when a compound of the present invention is added to a known liquid crystal material having a positive dielectric anisotropy.

A liquid crystal material selected as a basic material in the following use examples consisted of

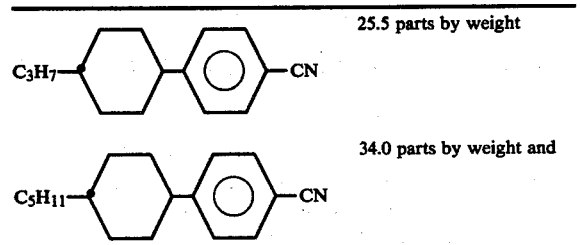

25.5 parts by weight 34.0 parts by weight and

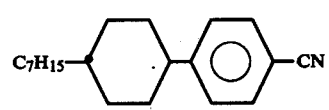

25.5 parts by weight.

This material will hereinafter be abbreviated to "Mixture A". The specific properties of liquid crystal compositions obtained by adding a compound of the present invention to Mixture A are shown in Table 2 together with those of Mixture A itself. In this Table, any of parts are by weight. Compound Nos. are the same as those in Table 1. $\eta_{20}$ represents viscosity coefficient at 20° C.; $\Delta\epsilon$, value of dielectric anisotropy; $\epsilon_{\parallel}$, dielectric constant in the direction of major axis; $\epsilon_{\perp}$, dielectric constant in the direction of minor axis; and Vth and Vsat, threshold voltage and saturation voltage of response at 20° C. in a twisted nematic display, respectively. The cell gap of the liquid cell used is 10 $\mu$m.

TABLE 2

| Example No. | Composition | | Nematic temperature range | $\eta_{20}$ (cp) | $\Delta\epsilon$ ($\epsilon_{\parallel}$; $\epsilon_{\perp}$) | Vth (V) | Vsat (V) |
|---|---|---|---|---|---|---|---|
| | Mixture A | | −3°~52.5° C. | 23.0 | 11.3 (16.2; 4.9) | 1.50 | 2.20 |
| 57 | Mixture A, Compound No. 2, | 90 parts 10 parts | −3°~61.5° C. | 30.3 | 12.5 (17.4; 4.9) | 1.51 | 2.15 |
| 58 | Mixture A, Compound No. 6, | 90 parts 10 parts | −2°~70.3° C. | 32.0 | 12.4 (17.1; 4.7) | 1.61 | 2.20 |
| 59 | Mixture A, Compound No. 7, | 85 parts 15 parts | −3°~59.2° C. | 39.7 | 15.6 (21.0; 5.4) | 1.31 | 1.80 |

TABLE 2-continued

| Example No. | Composition | | Nematic temperature range | $\eta_{20}$ (cp) | $\Delta\epsilon$ ($\epsilon_\parallel$; $\epsilon_\perp$) | Vth (V) | Vsat (V) |
| --- | --- | --- | --- | --- | --- | --- | --- |
| 60 | Mixture A, Compound No. 18, | 90 parts 10 parts | −3°∼56.3° C. | 27.0 | 11.6 (16.5; 4.9) | 1.45 | 1.99 |
| 61 | Mixture A, Compound No. 19, | 90 parts 10 parts | −3°∼53.8° C. | 27.3 | 11.4 (16.4; 5.0) | 1.44 | 1.98 |
| 62 | Mixture A, Compound No. 26, | 85 parts 15 parts | −3°∼54.9° C. | 32.0 | 10.1 (15.1; 5.0) | 1.53 | 2.10 |
| 63 | Mixture A, Compound No. 45, | 85 parts 15 parts | −2°∼75.2° C. | 34.3 | 10.2 (14.8; 4.6) | 1.70 | 2.32 |

What is claimed is:

1. 4-(Trans-4'-alkyloxymethylcyclohexyl)benzoic acid esters having the general formula

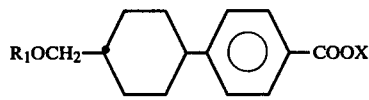   (I)

wherein X represents

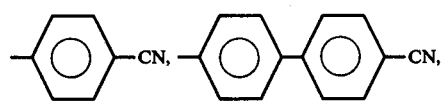

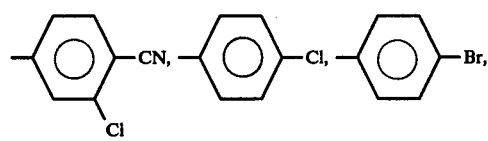

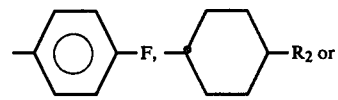

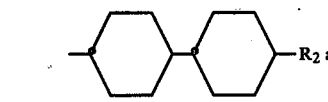 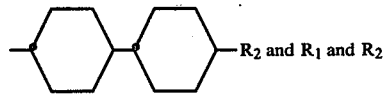 $R_2$ and $R_1$ and $R_2$ each represent an alkyl group of 1 to 10 carbon atoms.

2. Esters according to claim 1, expressed by the general formula

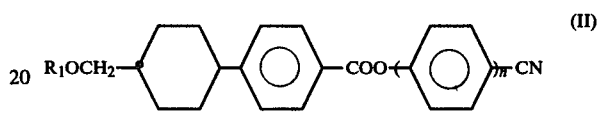   (II)

wherein n represents 1 or 2.

3. Esters according to claim 1, expressed by the general formula

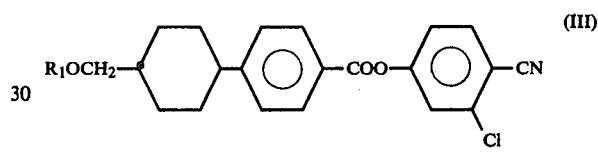   (III)

4. Esters according to claim 1, expressed by the general formula

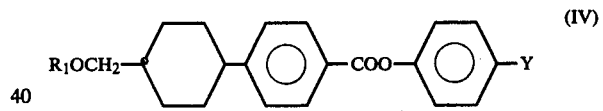   (IV)

wherein Y represents F, Cl or Br.

5. Esters according to claim 1, expressed by the general formula

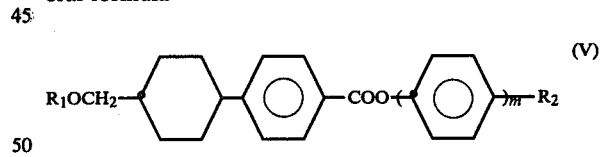   (V)

wherein m represents 1 or 2.

6. A liquid crystal composition comprising a mixture of compounds at least one of which is a compound according to claim 1.

* * * * *

UNITED STATES PATENT AND TRADEMARK OFFICE
CERTIFICATE OF CORRECTION

PATENT NO. : 4,452,719
DATED : June 5, 1984
INVENTOR(S) : INOUE et al

It is certified that error appears in the above—identified patent and that said Letters Patent is hereby corrected as shown below:

On the title page Inventors should read

[75]  Inventors:  Hiromichi Inoue; Takashi Inukai;
                  Yasuyuki Goto; Hideo Sato;
                  Masahiro Fukui, all of Kanagawaken,
                  Japan Signed and Sealed this Twenty-sixth Day of March 1985

[SEAL]

Attest:

DONALD J. QUIGG

Attesting Officer

Acting Commissioner of Patents and Trademarks